US010533959B2

United States Patent
Wiener et al.

(10) Patent No.: US 10,533,959 B2
(45) Date of Patent: Jan. 14, 2020

(54) DEVICE AND RELATED METHOD FOR SOLUTION SCATTERING AND DIFFRACTION SAMPLE HOLDERS

(71) Applicant: University of Virginia Patent Foundation, Charlottesville, VA (US)

(72) Inventors: Michael C. Wiener, Charlottesville, VA (US); Peter Horanyi, Seattle, WA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 408 days.

(21) Appl. No.: 15/029,992

(22) PCT Filed: Oct. 17, 2014

(86) PCT No.: PCT/US2014/061263
§ 371 (c)(1),
(2) Date: Apr. 15, 2016

(87) PCT Pub. No.: WO2015/058162
PCT Pub. Date: Apr. 23, 2015

(65) Prior Publication Data
US 2016/0238542 A1 Aug. 18, 2016

Related U.S. Application Data

(60) Provisional application No. 61/892,892, filed on Oct. 18, 2013.

(51) Int. Cl.
*G01N 23/083* (2018.01)
*G01N 23/20025* (2018.01)
(Continued)

(52) U.S. Cl.
CPC ............ *G01N 23/083* (2013.01); *B01L 3/505* (2013.01); *B01L 9/00* (2013.01); *B01L 9/52* (2013.01);
(Continued)

(58) Field of Classification Search
CPC .. G01N 1/00; G01N 1/02; G01N 1/10; G01N 1/28; G01N 2021/0106; G01N 2021/0321;
(Continued)

(56) References Cited

U.S. PATENT DOCUMENTS 3,218,459 A 11/1965 Bens
3,859,528 A * 1/1975 Luitwieler, Jr. ........... G01T 7/08
250/328
(Continued)

FOREIGN PATENT DOCUMENTS

WO WO 2013/025737 2/2013

OTHER PUBLICATIONS

Kalinin et al., "Crystal growth in X-ray-transparent plastic tubing: an alternative for high-throughput applications", Acta Crystallographica Section D, Nov. 2005, pp. 1528-1532, vol. D61, Part 11, Published by the International Union of Crystallography.
(Continued)

*Primary Examiner* — Anastasia Midkiff
(74) *Attorney, Agent, or Firm* — Robert J. Decker

(57) ABSTRACT

A sample holding device and related method designed to facilitate inexpensive and reliable testing of materials or specimens with beam diffraction and scattering techniques. The device features a sample receptacle that is made out of a polymer, cellulose, polymeric material, or cellulosic material. The flexible nature and low melting point of the sample receptacle allows for reliable sealing against the vacuum or gaseous environment used for beam diffraction or scattering analysis. The sample holding device can be considered disposable because of its low cost, eliminating the need for complex or unreliable cleaning procedures.

38 Claims, 10 Drawing Sheets

(51) Int. Cl.
*B01L 9/00* (2006.01)
*B01L 3/00* (2006.01)

(52) U.S. Cl.
CPC .... *G01N 23/20025* (2013.01); *B01L 2300/12* (2013.01); *B01L 2300/123* (2013.01); *G01N 2223/637* (2013.01)

(58) Field of Classification Search
CPC ... G01N 2021/0357; G01N 2021/0367; G01N 2021/0375; G01N 2021/135; G01N 2021/4738; G01N 2021/4788; G01N 2001/002; G01N 2001/1056; G01N 2001/1062; G01N 2001/2893; G01N 21/01; G01N 21/03; G01N 21/11; G01N 21/13; G01N 21/47; G01N 23/00; G01N 23/20; G01N 23/20008; G01N 23/20025; G01N 23/2003; G01N 23/201; G01N 23/2055; G01N 23/207; G01N 23/2076; G01N 2201/00; G01N 2201/02; G01N 2201/021; G01N 2201/022; G01N 2201/0221; G01N 2201/0222; G01N 2201/0224; G01N 2201/0227; G01N 2201/0228; G01N 2201/024; G01N 2201/0245; G01N 2201/04; G01N 2201/0415; G01N 2201/0438; G01N 2201/103; G01N 2223/00; G01N 2223/05; G01N 2223/054; G01N 2223/056; G01N 2223/30; G01N 2223/307; G01N 2223/309; G01N 2223/637; G01N 2223/639; G01N 2223/64; G01N 35/00; G01N 35/02; G01N 35/025; G01N 35/026; G01N 35/04; G01N 2035/00178; G01N 2035/00277; G01N 2035/00326; G01N 2035/0401; G01N 2035/0403; G01N 2035/0406; G01N 2035/0412; G01N 2035/0413; G01N 2035/0439; G01N 2035/0441; G01N 2035/0444; G01N 2035/0446; G01N 2035/0496; G01T 7/00; G01T 7/02; G01T 7/08; G01T 7/10; B01L 3/00; B01L 3/50; B01L 3/505; B01L 3/508; B01L 3/5085; B01L 9/00; B01L 2200/00; B01L 2200/02; B01L 2200/025; B01L 2200/028; B01L 2200/06; B01L 2200/0689; B01L 2300/00; B01L 2300/08; B01L 2300/0832; B01L 2300/0861; B01L 2300/087; B01L 2300/16; B01L 2300/168
See application file for complete search history.

(56) References Cited

U.S. PATENT DOCUMENTS

| | | | | |
|---|---|---|---|---|
| 4,244,458 | A * | 1/1981 | Kampf | G01T 7/08 198/346.2 |
| 4,643,033 | A * | 2/1987 | Solazzi | G01N 23/2204 356/246 |
| 5,656,807 | A * | 8/1997 | Packard | H01J 43/246 250/214 VT |
| 5,762,874 | A * | 6/1998 | Seaton | G01N 21/13 198/465.2 |
| 2005/0063867 | A1 * | 3/2005 | Moor | B01L 3/505 422/82.05 |
| 2011/0135990 | A1 | 6/2011 | Yamamoto | |
| 2012/0322052 | A1 * | 12/2012 | Halverson | G01N 1/18 435/5 |
| 2013/0101091 | A1 | 4/2013 | Garvey | |
| 2014/0234949 | A1 * | 8/2014 | Wasson | G01N 35/1065 435/287.2 |

OTHER PUBLICATIONS

Koch, et al., "Small-angle scattering: a view on the properties, structures and structural changes of biological macromolecules in solution", Quarterly Reviews of Biophysics, 2003, pp. 147-227, vol. 36, No. 2, Cambridge University Press.

Lipfert, et al., "Sample holder for small-angle x-ray scattering static and flow cell measurements", Review of Scientific Instruments, 2006, pp. 046108-1-046108-3, vol. 77, No. 4, Published by AIP Publishing.

Putman, et al., "X-ray solution scattering (SAXS) combined with crystallography and computation: defining accurate macromolecular structures, conformations and assemblies in solution", Quarterly Reviews of Biophysics, 2007, pp. 191-285, vol. 40. No. 3, Cambridge University Press.

Soliman, et al., "Development of high-performance X-ray transparent crystallization plates for in situ protein crystal screening and analysis", Acta Crystallographica Section D, Jul. 2011, pp. 646-656, vol. D67, Part 7, Published by the International Union of Crystallography.

Toft, et al., "High-Throughput Small Angle X-ray Scattering from Proteins in Solution Using a Microfluidic Front-End", Analytical Chemistry, May 2008, pp. 3648-3654, vol. 80, No. 10, Published by ACS Publications.

* cited by examiner

DEVICE AND RELATED METHOD FOR SOLUTION SCATTERING AND DIFFRACTION SAMPLE HOLDERS

CROSS-REFERENCE TO RELATED APPLICATIONS

The present application is a national stage filing of International Application No. PCT/US2014/061263, filed Oct. 17, 2014, which claims benefit of priority under 35 U.S.C. § 119(e) from U.S. Provisional Application Ser. No. 61/892,892, filed Oct. 18, 2013, entitled "Device and Related Method for X-Ray Scattering Sample Holders;" the disclosures of which are hereby incorporated by reference herein in their entirety.

STATEMENT OF GOVERNMENT INTEREST

This invention was made with government support under Grant No. GM094611, awarded by the National Institutes of Health. The government has certain rights in the invention.

FIELD OF THE INVENTION

The present invention relates generally to the field of beam scattering and diffraction. More specifically, the invention relates to the subfields of x-ray crystallography and x-ray solution scattering and diffraction, and the equipment used therein.

BACKGROUND

Beam scattering and diffraction are useful analytical tools used by researchers to determine the size, structure, and properties of molecules or other very small structures. Beam scattering and diffraction involve the use of an energy source that produces a beam, usually of x-rays, though other wavelengths or particle beams may also be used. The beam is passed through a sample, which is entrained in a receptacle. The beam is diffracted in the sample, and then continues on to a detector which reads the scattered or diffracted beam. Researchers are then able to determine properties of the material sample and reconstruct aspects of its structure, such as molecular weight, size, and composition. When the sample consists of spatially uncorrelated or disordered particles, such as atoms or molecules, the interaction of light or a beam with said sample is called scattering. When the sample consists of spatially correlated or ordered particles, such as atoms or molecules, the interaction of light or a beam with said sample is called diffraction.

Researchers are currently forced to use quartz or capillary tubes that entrain the sample to be tested, particularly in the case of solution scattering analysis. However, these types of tubes have a number of drawbacks, which make solution scattering analysis expensive, difficult, or impractical. Glass or quartz capillaries, often part of other complex sample containment assemblies, are costly, easily broken, and difficult to seal. Notably, the glass or quartz capillaries cannot be self sealed because the heat required to melt the capillary tube is so high that it would damage or degrade most sample materials, particularly liquids. Furthermore, glass or quartz capillaries may prevent the testing of certain difficult to procure samples, because sample recovery may be complex or impossible with existing sample receptacles. Also, because of their significant cost, glass or quartz capillaries are not disposable, requiring unreliable and time consuming cleaning steps which may lead to the contamination of subsequent samples from incomplete removal of previous samples or the cleaning fluids themselves.

There is a need in the art for a sample holding device which is inexpensive, robust, easy to manufacture, reduces contamination, and which allows for recovery of the working sample.

OVERVIEW

Beam scattering and diffraction techniques are very useful to researchers attempting to analyze the molecular structure of a specimen. Oftentimes these techniques are not used because of the difficulty of testing specimens, particularly in liquid phase, with existing testing equipment. However, the use of an embodiment of the present invention polymer, polymeric, cellulose, or cellulosic sample receptacle shall improve the beam scattering and diffraction testing processes and make it more viable across a wider range of potential applications.

An aspect of an embodiment of the present invention device and its associated method provides, among other things, the user with an inexpensive, easy to use, and effective sample holding device. In one aspect, an embodiment of the device utilizes, for example, a polymer, polymeric material, cellulose, or cellulosic material for a sample receptacle. A number of advantages result from this change in material. The polymer, cellulose, polymeric, or cellulosic sample receptacles are much less expensive and do not easily shatter like quartz or glass tubes. Furthermore, polymer, cellulose, polymeric, or cellulosic sample receptacles can be easily mass-produced so that researchers may dispose of the sample receptacle after a single use. This greatly simplifies the beam scattering and diffraction testing processes because no cleaning between specimens is required, eliminating a time consuming step and the potential for contamination.

Using a polymer, cellulose, polymeric, or cellulosic sample receptacle also offers a number of advantages for sealing specimens in the sample receptacle. The more flexible and pliable nature of the sample receptacle of an embodiment of the present invention allows for, among other things, sealing that is more effective and reliable than methods used with glass or quartz tubes, for example. Additionally, another advantage of a polymer, cellulose, polymeric, or cellulosic material of an embodiment of the present invention is, but not limited thereto, that it has a melt temperature low enough to allow for heat sealing of the sample receptacle at temperatures that are not likely to damage or degrade specimens. This dramatically reduces the possibility of specimen loss, particularly when the beam scattering or diffraction test is carried out in a vacuum that could pull the specimen from the sample receptacle. It is also advantageous that the sample receptacle of an embodiment of the present invention may be sealed independently from any device or apparatus that may be used to hold the sample receptacle.

Another aspect of an embodiment of the present invention sample holding device is that recovery of the specimen is straightforward and reliable with a polymer, polymeric, cellulose, or cellulosic sample receptacle. Since polymers, polymeric materials, cellulose, or cellulosic materials are relatively soft and pliable, a specimen, especially if it is in liquid phase, may be recovered by piercing the sample receptacle material and drawing the specimen back out. This could be done with a syringe (or any applicable device) or by cutting the sample receptacle. Since the material is flexible and will not shatter, there is no chance of contamination due to small particles of broken glass or quartz remaining in the specimen. It is also possible to easily mold in or attach access apertures to the sample receptacle to facilitate deposit and removal of specimens (or other materials as desired or required) from the sample receptacle.

An aspect of an embodiment of the present invention provides, among other things, a device for use in solution scattering or diffraction. The device may comprise at least one sample receptacle comprising, at least in part, a polymer material, polymeric material, cellulose material, cellulosic material, or any combination thereof, the at least one sample receptacle configured to accommodate a sample; a retainer, the retainer configured to removably hold the at least one sample receptacle and allow for the at least one sample receptacle to be in communication with a scattering beam or diffraction beam; and wherein the at least one sample receptacle is configured to be sealable for containing the sample, wherein sealing is independent of the retainer.

An aspect of an embodiment of the present invention provides, among other things, a method for solution scattering or diffraction. The method may method comprise: providing at least one sample receptacle comprising, at least in part, a polymer material, polymeric material, cellulose material, cellulosic material, or any combination thereof, the at least one sample receptacle accommodating a sample; holding the at least one sample receptacle and allowing for the at least one sample receptacle to be in communication with a scattering beam or diffraction beam; and sealing the at least one sample receptacle for containing the sample.

An aspect of an embodiment of the present invention provides, among other things, a method for solution scattering or diffraction. The method may comprise: providing at least one sample receptacle comprising, at least in part, a polymer material, polymeric material, cellulose material, cellulosic material, or any combination thereof, the at least one sample receptacle configured to accommodate a sample; providing a retainer configured for holding the at least one sample receptacle and allowing for the at least one sample receptacle to be in communication with a scattering beam or diffraction beam; and the sample receptacle configured to allow the sample to be sealed in the at least one sample receptacle for containing the sample.

An aspect of an embodiment of the present invention provides, among other things, a method for solution scattering or diffraction. The method may comprise: providing at least one sample receptacle comprising, at least in part, a polymer material, polymeric material, cellulose material, cellulosic material, or any combination thereof, the at least one sample receptacle configured to accommodate a sample; wherein the at least one sample receptacle is configured to allow the at least one sample receptacle to be in communication with a scattering beam or diffraction beam; and the sample receptacle configured to allow the sample to be sealed in the at least one sample receptacle for containing the sample.

An aspect of an embodiment of the present invention provides, among other things, a sample holding device and related method designed to facilitate inexpensive and reliable testing of materials or specimens with beam diffraction and scattering techniques. An aspect of an embodiment of the present invention device features a sample receptacle that may be made out of a polymer, cellulose, polymeric material, or cellulosic material. The flexible nature and low melting point of the sample receptacle allows for reliable sealing against the vacuum or gaseous environment used for beam diffraction or scattering analysis. The sample holding device can be considered disposable because, among other things, of its low cost, thereby eliminating the need for complex or unreliable cleaning procedures. Using a polymer, polymeric material, cellulose, or a cellulosic material (or other like material selected as desired or required) prevents breakage of sample receptacles and allows for recovery of a specimen after beam scattering or diffraction testing is complete. The specific polymer, polymeric material, cellulose, or cellulosic material selected (or other material selection as desired or required) can be tailored to different wavelengths or beam types, blocking certain wavelengths while allowing others to pass through.

These and other objects, along with advantages and features of various aspects of embodiments of the invention disclosed herein, will be made more apparent from the description, drawings and claims that follow.

BRIEF DESCRIPTION OF THE DRAWINGS

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF EXEMPLARY EMBODIMENTS OF THE PRESENT INVENTION

Figure 1:
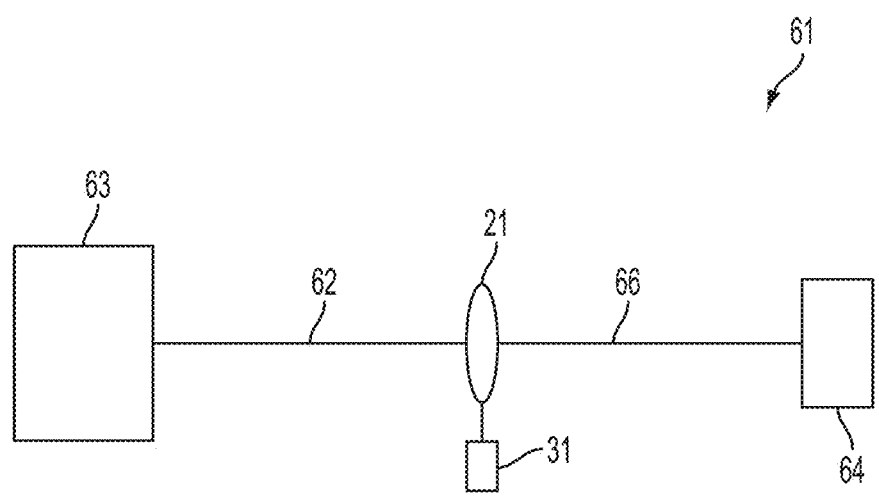
FIG. 1 provides a schematic illustration of an embodiment of the present invention being used in conjunction with an x-ray scattering system.

FIG. 1 provides a schematic depiction of an aspect of an embodiment of the present invention sample receptacle 21 and retainer 31 being used in conjunction with an x-ray scattering system 61. An energy source 63 generates an x-ray beam 62, which is aimed at the sample receptacle 21. The sample receptacle 21 is positioned between the energy source 63 and a detector 64 by a retainer 31. The x-ray beam 62 passes through the sample receptacle 21 and the sample, which is held therein. After exiting the sample receptacle 21, a scattered x-ray beam 66 is directed towards the detector 64 to be measured and analyzed. It should be appreciated that this schematic illustration shows a general arrangement of the sample receptacle 21 and retainer 31 being used in conjunction with the x-ray scattering system 61. The sample receptacle 21 and retainer 31 may take on various different forms, as may the x-ray scattering system 61. Furthermore, it should be appreciated that the sample receptacle 21 and retainer 31 may be used with numerous different types of systems which may incorporate x-rays, gamma rays, ultraviolet light, visible light, infrared light, or any other wavelength or frequency of the electromagnetic spectrum that may be desired or required by the user.

Figure 2:
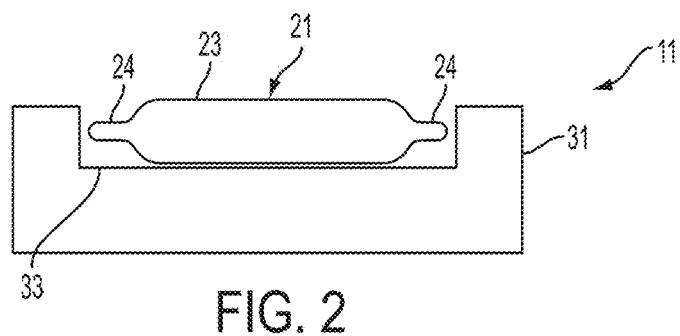
FIG. 2 provides a schematic illustration of an embodiment of the present invention sample holding device.

FIG. 2 provides a schematic illustration of an embodiment of the present invention sample holding device 11. The device 11 may be comprised of a sample receptacle 21 that is located on or within a retainer 31. The sample receptacle 21 may be configured with a compartment 23 that is suited for retaining a sample to be tested. It should be appreciated that the sample receptacle 21 is manufactured from, or otherwise made from, at least in part, a polymer material, a polymeric material, a cellulose material, a cellulosic material, or any combination thereof. It should be appreciated that the sample receptacle 21 may be manufactured from other materials as desired or required to meet the operational and structural demands. For example, but not limited thereto, the sample receptacle 21 may comprised of any material that provides for the flexible and pliable nature of the sample receptacle 21. The sample receptacle 21 may have seals 24 which contain the sample (not shown) within the compartment 23 of the sample receptacle 21. These seals 24, of which there may be one, two, or more as desired, required or needed, may be achieved in any number of different ways so as to suit the needs of a particular application. For example, the seals 24 may comprise any number of different methods including heat seals, mechanical seals, such as clips, pins, clamps, or other mechanical sealing means, adhesion seals, such as glue, epoxy, or through other bonding agents, or chemical seals including chemicals that may melt or otherwise close the ends of the sample receptacle 21. It may also be desirable to use liquids that may be applied to the ends of the sample receptacle that dry in place to form a plug or seal that will serve to contain a sample in the sample receptacle 21. It should be appreciated that, because of the choice of a polymer, polymeric, cellulose, or cellulosic material for the sample receptacle 21, heat sealing methods may be considered preferable in a number of applications. Specifically, the sample receptacle 21, made of the aforementioned materials, may have heat applied to the ends to melt the sample receptacle 21 to create seals 24. This method of sealing may be preferable for a number of applications because it is inexpensive, secure, easy to achieve even on small sample receptacles, and should not require so much heat as to damage or degrade the sample entrained within the sample receptacle 21. It should be appreciated that the sample receptacle may take on all shapes along the entire continual geometric spectrum of manipulation of x, y and z planes for containing a sample during any stage of its use, as well as being configured to be secured appropriately during any stage of use. For example, some exemplary shapes of the sample receptacle may include, but not limited thereto, spherical, cubical, cuboid, prismatic, pyramidal, tubular, or cylindrical, as well as any combinations thereof.

Still referring to FIG. 2, the retainer 31 is depicted with a cavity 33. This cavity, which may take on any number of shapes or forms including, but not limited to, a channel, aperture, depression, crease, opening, or slot is configured to removably hold at least one sample receptacle 21 and allow for the sample receptacle 21 to be in communication with an energy beam. The sample receptacle 21 may be held in place in the retainer 31 by any number of means including, but not limited to, mechanical attachments, friction fit retention, interference fit retention, magnetic retention, or adhesive retention. It should be appreciated that retention means such as clips, snap fittings, or hook and loop fasteners may be used to achieve retention of the sample receptacle 21 in the cavity 33 of retainer 31.

Figure 3:
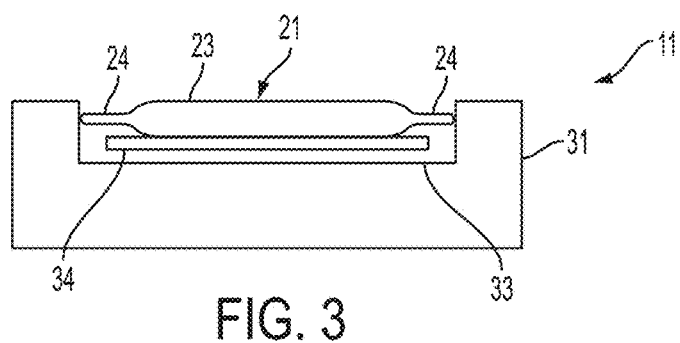
FIG. 3 provides a schematic illustration of an embodiment of the present invention sample holding device incorporating an adapter or insert.

FIG. 3 provides a schematic illustration of an aspect of an embodiment of the present invention sample holding device 11 incorporating an adapter or insert 34 or the like. Once again, the device 11 may be configured with a sample receptacle 21 which is comprised of a compartment 23 and seals 24 to contain the sample (not shown). The sample receptacle 21 may be held or placed within the cavity 33 of the retainer 31. The sample receptacle 21 is in communication with an adapter or insert 34, which is likewise in communication with the retainer 31. The sample receptacle 21 may be held or retained by the adapter or insert 34 by any number of attachment or retention means, including, but not limited to, a friction fit, interference fit, snap fits, clips, magnets, hook and loop fasteners, adhesives, or any other attachment or retention means as desired, required, or needed by the particular application. Furthermore, an adapter or insert may include other attachment or retention means including wedges, clay, foam, wax, or any other secure attachment. The adapter or insert 34 is configured so as to facilitate the mating of the sample receptacle 21 and the retainer 31. It should be appreciated that multiple types or configurations of adapter or insert 34 may be used with a single retainer 31 to accommodate any number of different sample receptacle 21 configurations, or vice versa. In this particular schematic illustration, the adapter or insert 34 is shown positioned lengthwise with the sample receptacle 21, however this is only an illustrative example, and the adapter or insert 34 may be oriented transversely, at the ends, along the sides, or in any other relation to the sample receptacle 21. Furthermore, although not shown, it should be appreciated that the adapter or insert 34 may be configured to be used as a door, lid, latch, cross-member, or hatch to enclose the sample receptacle 21 within the cavity 33 of the retainer 31.

Figure 4:
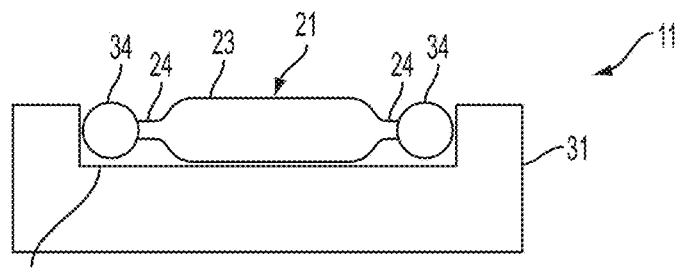
FIG. 4 provides a schematic illustration of an embodiment of the present invention sample holding device incorporating multiple adapters or inserts.

FIG. 4 provides a schematic illustration of an aspect of an embodiment of the present invention sample holding device 11 incorporating multiple adapters or inserts 34. Once again, the device 11 is shown having a sample receptacle 21 with a compartment 23 configured to hold a sample (not shown) and seals 24 configured to retain the sample in the compartment 23. Multiple adapters or inserts 34 are shown located in communication with the seals 24 and the cavity 33 of the retainer 31. Here, again, the adapters or retainers 34 may take on any number of attachment or retention means, including, but not limited to, a friction fit, interference fit, snap fits, clips, magnets, hook and loop fasteners, adhesives, or any other attachment or retention means as desired, required, or needed by the particular application. Furthermore, an adapter or insert may include other attachment or retention means including wedges, clay, foam, wax, or any other secure attachment. It should be appreciated that the adapters or inserts 34 may be disposed, located, or arranged in any relationship to either the sample receptacle 21 or the retainer 31. For example, the adapters or inserts 34 may be arranged at the ends of the sample receptacle 21, along the sides, laterally, longitudinally, transversely, parallel to the sample receptacle 21, or in any other relation as desired or required for any particular application. The adapters or inserts 34 are configured so as to facilitate the mating of the sample receptacle 21 and the retainer 31. It should be appreciated that multiple types or configurations of adapters or inserts 34 may be used with a single retainer 31 to accommodate any number of different sample receptacle 21 configurations, or vice versa. For example, although not shown, the multiple adapters or inserts 34 may be located in communication with the sample receptacle without being in communication with the seals 24. Alternatively, although not shown, the multiple adapters or inserts 34 may be located in communication with the sample receptacle while being in communication with both the seals 24 as well as other portions of the sample receptacle 21.

Figure 5:
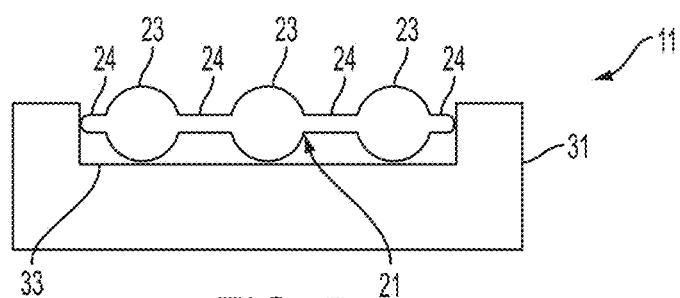
FIG. 5 provides a schematic illustration of an embodiment of the present invention sample holding device with multiple compartments.

FIG. 5 provides a schematic illustration of an aspect of an embodiment of the present invention sample holding device 11 with a sample receptacle 21 which is comprised of multiple compartments 23 for holding multiple samples (not shown) which are separated and bound by multiple seals 24. The sample receptacle 21 is located within the cavity 33 of the retainer 31. It should be appreciated that the sample receptacle 21 may have as many compartments 23 as necessary or practical for any particular application. Furthermore, the compartments 23 may be arranged in any way as desired or required by the user, and is not limited to compartments that are linearly disposed. The sample receptacle 21 may be configured to allow for compartments 23 to be arranged in a closed shape, such as a circle, square, rectangular, polygonal, elliptical, or other shape as necessary. It should be appreciated that any of the aforementioned methods for creating seals 24 and attaching or retaining the sample receptacle 21, with or without an adapter or insert, would be viable for a sample receptacle 21 with multiple compartments 23. It should be appreciated, in an alternative embodiment, that seals are not provided between compartments so as to allow flow or transfer of samples or other materials between the compartments as desired or required. Accordingly, for example, a type of transfer path or transfer area would be provided between the compartments to accommodate the movement or flow of the sample or other material.

Figure 6:
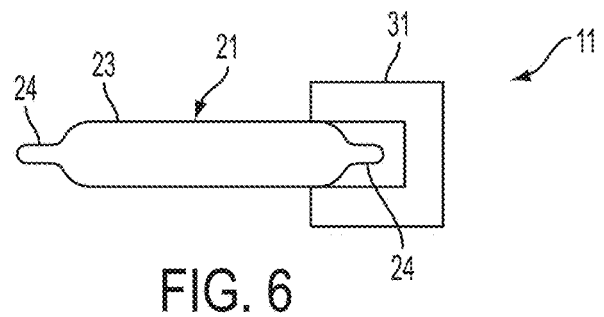
FIG. 6 provides a schematic illustration of an embodiment of the present invention sample holding device with a retainer at one end.

FIG. 6 provides a schematic illustration of an aspect of an embodiment of the present invention sample holding device 11 with a retainer 31 located at one end of the sample receptacle 21. The sample receptacle 21, including the compartment 23 and seals 24 for containing a sample (not shown), is located and retained by a retainer 31 at one end of the sample receptacle 21. It should be appreciated that the retainer 31 may be located at either end of the sample receptacle 21, and that the retainer 31 may be configured or arranged so as to hold the sample receptacle 21 vertically, horizontally, or at any angle as desired, required, or needed.

Figure 7:
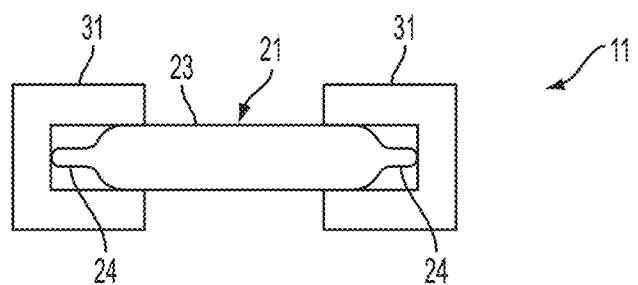
FIG. 7 provides a schematic illustration of an embodiment of the present invention sample holding device with multiple retainers.

FIG. 7 provides a schematic illustration of an aspect of an embodiment of the present invention sample holding device 11 with multiple retainers 31. The sample receptacle 21, including compartment 23 and seals 24 for containing a sample (not shown), is located and retained by multiple retainers 31 at either end of the sample receptacle 21. It should be appreciated that the retainers 31 may be located at any location on the sample receptacle 21, and that the retainers 31 may be configured or arranged so as to hold the sample receptacle 21 vertically, horizontally, or at any angle as desired, required, or needed. It should be appreciated that more than two retainers 31 may be implemented.

Figure 8:
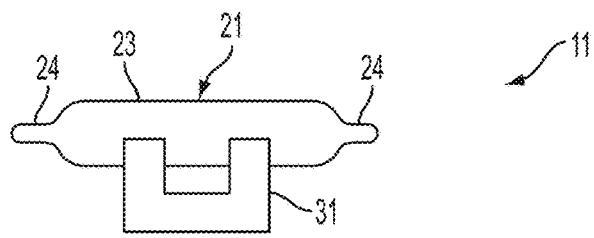
FIG. 8 provides a schematic illustration of an embodiment of the present invention sample holding device with a centrally located retainer.

FIG. 8 provides a schematic illustration of an aspect of an embodiment of the present invention sample holding device 11 with a centrally located retainer 31. The retainer 31 locates and retains the sample receptacle 21, including the compartment 23 and seals 24. The retainer 31 is shown holding or retaining the sample receptacle 21 from a substantially central location. It should be appreciated that the retainer 31 may be configured or arranged so as to hold the sample receptacle 21 vertically, horizontally, or at any angle as desired, required, or needed. It should be appreciated that the retainer 31 (or more than one retainer) may be located at any point along any side or portion of a sample receptacle 21 per sample receptacle 21.

Figure 9:
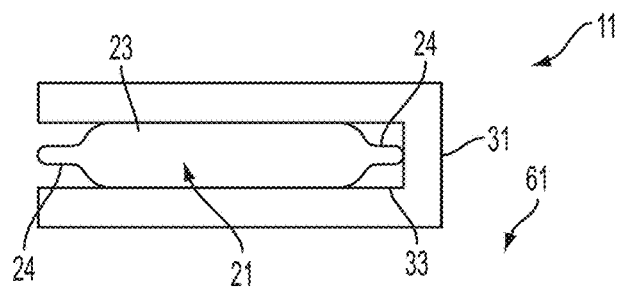
FIG. 9 provides a schematic illustration of an embodiment of the present invention sample holding device with a full length retainer at one end.

FIG. 9 provides a schematic illustration of an aspect of an embodiment of the present invention sample holding device 11 with a full length retainer 31. The sample receptacle 21 is located within the cavity 33 of the retainer 31. As shown, the retainer 31 has a cavity 33 configured to run parallel to the compartment 23 and seals 24. The retainer 31 may be configured to enclose all or any portion of the length of the sample receptacle 21 as is desired or required by the user to allow for locating the sample receptacle 21 as necessary.

It should be appreciated that the sample receptacle 21 may be manufactured or formed of a material that is compatible with the particular type of beam scattering, diffraction, or spectroscopy that is used. Material choice should account for such factors as the chemical properties of the samples to be tested to ensure there is no degradation of the sample or the sample receptacle 21, the temperatures and pressures that the testing (or analyzing, passing, accessing, or through-putting) will take place at, and the specific interaction of the material with the beam that will be used. In particular, it may be useful to select a material which is transparent or translucent to x-ray wavelengths of electromagnetic radiation. Other potential wavelengths that may be used in testing include gamma wavelengths, ultraviolet wavelengths, visible wavelengths, or infrared wavelengths. Beams composed of particles, such as electrons or neutrons, may also be used in conjunction with the present invention sample holding device, and their interaction with the particular material of choice should be considered. Said differently and by way of example, the material choice should allow for the particular beam that is to be used in testing to pass through the material of the sample receptacle 21 with as little interaction, hindrance, or absorption as possible to so as to allow the beam to interact principally with the sample entrained within. However, it should also be appreciated that it may be useful to select a material that is transparent or translucent to one wavelength of electromagnetic radiation or one type of beam, but that is opaque to another. For example, some samples may be sensitive or degraded by visible wavelengths of light, but the user may wish to test them with an x-ray beam. In this particular, non-limiting example, a material which is opaque to visible light but transparent or translucent to x-ray wavelengths would be desirable for that particular application.

For the preceding discussion of FIGS. 1-9, it should be appreciated that any parts, such as adapters or inserts, any means for attachment or retention, material selections, sealing means, locations of components, or other features described in one figure may be applied equally to any other figure shown. FIGS. 1-9 are given for exemplary purposes only, and are not limiting examples. Other configurations of retainer or sample receptacle may be used as desired or required to fit existing laboratory equipment (or yet to be designed laboratory equipment) and allow the usage of a sample receptacle that consists of a polymer, polymeric material, cellulose, cellulosic material, or any combination thereof. It should be appreciated that the related components or portions of the related components as discussed herein may take on all shapes along the entire continual geometric spectrum of manipulation of x, y and z planes to provide and meet the structural demands and operational requirements.

It should be appreciated that various sizes, dimensions, contours, rigidity, shapes, flexibility and materials of any of the components or portions of components in the various embodiments discussed throughout may be varied and utilized as desired or required.

Still referring to FIGS. 1-9, it should be appreciated that the sealing of the sample receptacle 21 may be achieved in any number of ways, both dependent upon the retainer 31 and independent of the retainer 31. As shown, the sample receptacle 21 may be sealed itself. However, it should be appreciated that the sample receptacle 21 may be sealed in such a way as to depend upon the retainer 31. For example, the sample receptacle may be sealed through the use of any one of the attachment or retention means mentioned above. The sample receptacle 21 may be bonded, glued, or melted into the retainer 31 to seal the compartment 23. It is also possible that the adapter or insert 34 may be used in such a way as to seal the sample receptacle 21 when the adapter or insert 34 is used to retain or attach the sample receptacle 21 to the retainer 31. Furthermore, the sample receptacle 21 may be used with or without a retainer 31, and in any of the preceding examples, the retainer is configured to removably hold or locate the sample receptacle 31. Said differently, the sample receptacle 21 may be inserted and removed from the retainer 31 to allow for the use of multiple sample receptacles 21 with a single retainer 31, or vice versa.

Figure 10:
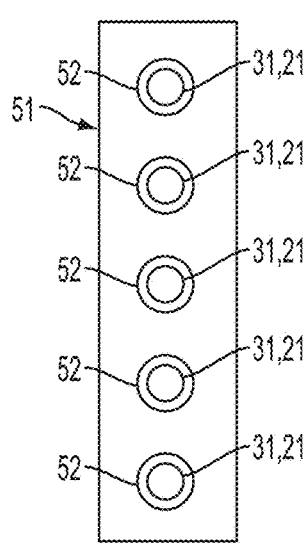
FIG. 10 provides a schematic illustration of multiple exemplary sample holding devices in a linear rack.

FIG. 10 provides a schematic illustration of an aspect of an embodiment of the present invention sample holding device located in a rack, such as a linear rack 51. The rack 51 may have multiple bays 52 which are configured to house one or more retainers 31 that house sample receptacles 21. Alternatively, it should be appreciated that the rack 51 and its constituent bays 52 may be configured so as to directly house one or more sample receptacles 21 without the need for retainers 31. The rack 51 may be configured to hold any number of retainers 31 or sample receptacles 21 as desired or required, from a minimum of one, up to any number as is practical for the equipment and space limitations of the laboratory where it is being used. Furthermore, it should be appreciated that the rack 51 may be composed of multiple linear sections, making it possible to arrange the bays 52 in a two dimensional array. This array may be in the form of a rectangle, square, polygon, closed curved shape, or any other shape that is practical for any particular application or testing apparatus.

Figure 11:
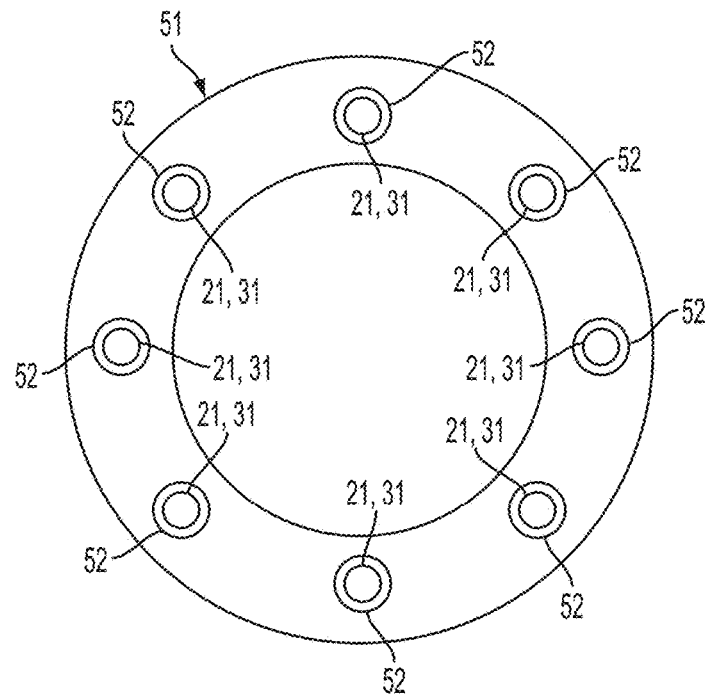
FIG. 11 provides a schematic illustration of multiple exemplary sample holding devices in a circular or rounded rack.

FIG. 11 provides a schematic illustration of an aspect of an embodiment of the present invention sample holding device located in a rack, such as a circular or round rack 51. The rack 51 may have one or multiple bays 52, which are configured to house retainers 31 that house sample receptacles 21. Alternatively, it should be appreciated that the rack 51 and its constituent bays 52 may be configured so as to directly house one or more sample receptacles 21 without the need for retainers 31. The rack 51 may be configured to hold any number of retainers 31 or sample receptacles 21 as desired or required, from a minimum of one, up to any number as is practical for the equipment and space limitations of the laboratory where it is being used. Furthermore, it should be appreciated that the rack 51 may be composed of multiple circular or rounded sections, concentric or otherwise, making it possible to arrange the bays 52 in a two dimensional array. The rack 51 may take on any number of geometries, including open or closed curved or curvilinear shapes. These curvilinear shapes may include, though not limited to, circular, semi-circular, oval, elliptical, parabolic, hyperbolic, or semi oval shapes.

It should be appreciated that the rack 51 may take on any number of geometries, including any three-dimensional shape, such as but not limited thereto, spherical, cubical, cuboid, prismatic, pyramidal, tubular, or cylindrical.

Figure 12:
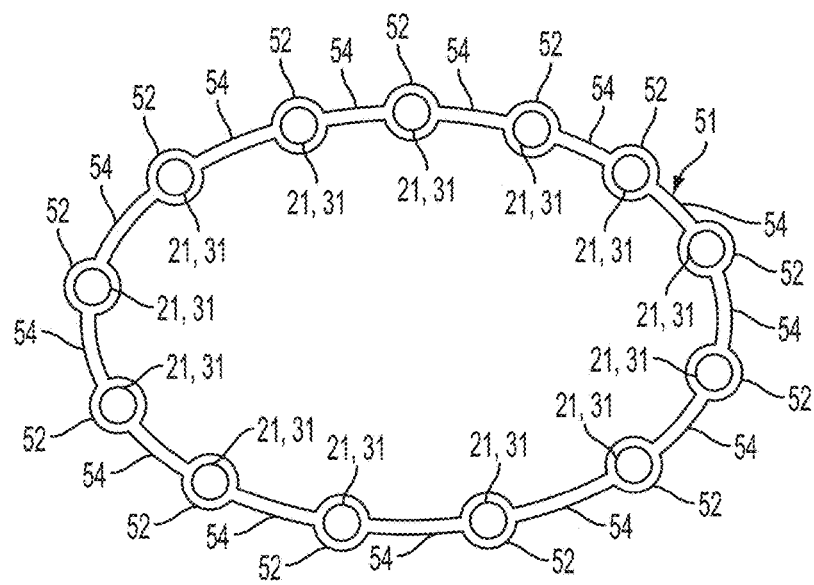
FIG. 12 provides a schematic illustration of multiple exemplary sample holding devices in a flexible or articulating rack.

FIG. 12 provides a schematic illustration of an aspect of an embodiment of the present invention sample holding device located in a rack, such as a flexible or articulating rack 51. The rack 51 may be composed of one or more bays 52, which are configured to house retainers 31 that house sample receptacles 21. Alternatively, it should be appreciated that the rack 51 and its constituent bays 52 may be configured so as to directly house one or more sample receptacles 21 without the need for retainers 31. Disposed between the bays 52 are multiple flexible or hinged members 54. These flexible or hinged members 54 allow the bays 52 to articulate or move relative to one another. This allows the rack 51 to function as a chain or magazine of sample receptacles 21 to allow for rapid testing (or analyzing, passing, accessing, or through-putting) of multiple samples while allowing for continuous removal and replacement of sample receptacles 21, and optionally their retainers 31. Said differently, the flexible or articulating rack 51 allows for one sample receptacle 21 to be located in the test chamber, tested, and then a movement or rotation of the rack 51, as if it were a chain or belt, to move another sample receptacle 21 into place for further testing (or analyzing, passing, accessing, or through-putting). While this motion takes place, other bays 52 may be located outside of the testing area, allowing sample receptacles 21 or retainers 31 to be removed and replaced in the rack 51, allowing for continuous testing (or analyzing, passing, accessing, or through-putting) of a number of samples greater than the number of bays 52 in the rack 51. It should be appreciated that the rack 51 may have any number of bays as desired or required, including the ability to add or subtract bays as modular elements. Furthermore, the flexible or hinged members 54 may be composed of flexible materials, such as wires, rubber components, elastomeric components, or any other material that easily deflects, or they may be made of hinged rigid components as with a chain.

The preceding discussion of FIGS. 10-12 serves to illustrate the fact that the sample receptacles 21 and their optional retainers 31 may be particularly well suited to testing (or analyzing, passing, accessing, or through-putting) large numbers of samples in a relatively short period of time. The preceding discussion of FIGS. 10-12 serves to illustrate the fact that the sample receptacles 21 and their optional retainers 31 may be particularly well suited to testing (or analyzing, passing, accessing or through-putting) large numbers of samples in a relatively automated and efficient manner. Because the sample receptacles 21 are composed of a polymer, polymeric material, cellulose, cellulosic material, or any combination thereof, the sample receptacles 21 are inexpensive, easy to manufacture in great numbers, and easy to load and seal quickly and reliably allowing for testing (or analyzing, passing, accessing, or through-putting) many more samples than would be possible with glass or quartz based components. Furthermore, it should be appreciated that the recovery of the sample from the sample receptacle 21 would be comparatively simple because the nature of the polymer, polymeric material, cellulose, or cellulosic material is such that the sample could easily be recovered either through use of a syringe or other removal or extraction tool or device, or through cutting or tearing the sample receptacle 21 to allow removal of the sample without contamination or degradation. This advantage allows for samples that are very difficult to prepare in large quantities to be tested through beam scattering and diffraction methods without the drawback of potential sample loss due to the use of glass or quartz components. Furthermore, it should be appreciated that the inexpensive and easy to use nature of the present invention sample holding device allows for the sample receptacle 21 to be a disposable device, reducing the need for constant cleaning and repair of laboratory equipment. It should also be appreciated that the retainer 31 and any other parts of the invention may be made from inexpensive materials that are conducive to mass production allowing for virtually any part of the device or invention to be made in large quantities. Consequently, the device and its associated parts may be disposable and offer further advantages over a glass or quartz component.

Figure 13:
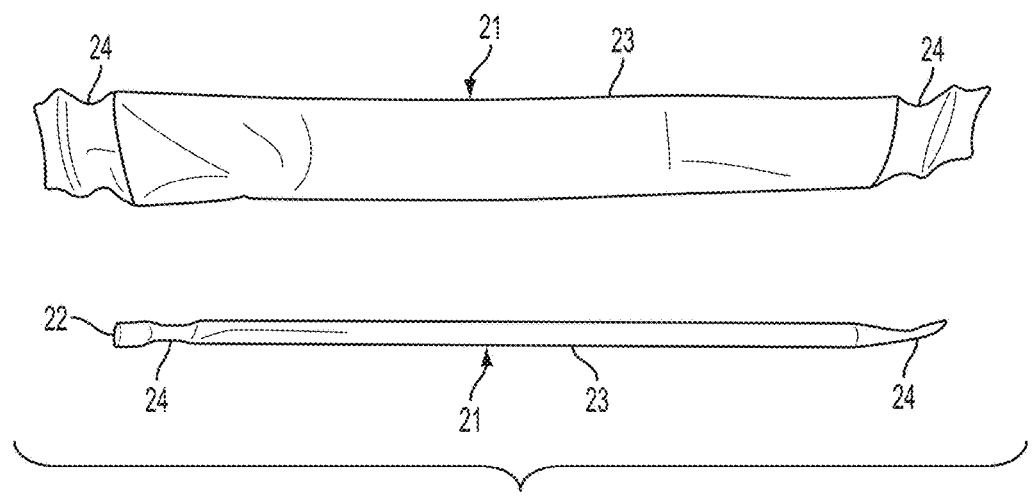
FIG. 13 provides a schematic illustration of exemplary embodiments of the present invention sample holding device sample receptacles.

FIG. 13 provides a schematic illustration of an aspect of an embodiment of the present invention sample holding device sample receptacles 21. As shown, the sample receptacle 21 may take any number of shapes or sizes as desired or required. In particular, a larger sample receptacle 21 (illustrated at the top of the figure relative to the bottom of the figure) may be used for samples (not shown) which are larger or easy to procure, while smaller sample receptacles 21 (illustrated at the bottom of the figure relative to the top of the figure) may be used for samples (not shown) which are harder to procure or produce. Regardless of the shape or size, the sample receptacle 21 will be comprised of a compartment 23 and one or more seals 24. Optionally, the sample receptacle 21 may include one or more access apertures 22 which allows for insertion and removal of the sample from the compartment or compartments 23. This access aperture 22 may be a one way valve, a diaphragm which may be pierced by a syringe and self seal upon retraction of the syringe, a fitting, or any other device which would allow for insertion and removal of the sample. It should be appreciated that the access aperture 22 may be configured to be integral with the sample receptacle 21 or it may be manufactured as a separate part that is attached to the sample receptacle 21 with an adhesive, press joint, threaded joint, interference fit, or any other means or method of attachment, securing, or anchoring as desired or required.

Figure 14:
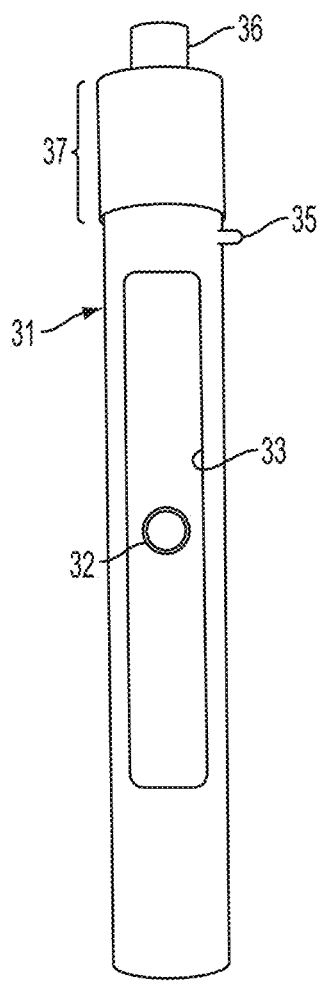
FIG. 14 provides a schematic illustration of an exemplary embodiment of the present invention sample holding device retainer.

FIG. 14 provides a schematic illustration of an aspect of an embodiment of the present invention sample holding device retainer 31. This retainer 31 is shown for illustrative purposes and is only one of many possible configurations for a retainer 31 that may be used to replace existing retainers or sample holders in existing laboratory equipment (as well as other or future designed laboratory equipment). The retainer 31 includes a cavity 33 that is configured to accept a sample receptacle (not shown). Within the cavity 33 is a wavelength access aperture 32 which allows the scattering or diffraction beam to pass through the retainer 31 and intersect with the sample receptacle (not shown). It should be appreciated that the sample receptacle would be aligned with the wavelength access aperture 32 to allow the scattering or diffraction beam to pass through the sample receptacle and the sample. This specific, non-limiting, example of a retainer 31 is fitted with an alignment pin 35 and an alignment cap 37 to allow the retainer 31 to work with a specific piece of laboratory equipment used in beam scattering or diffraction techniques. The retainer 31 also includes a retrieval pin 36 to allow for easy removal of the retainer 31 from a laboratory apparatus. It should be appreciated that the retainer 31 may take on any configuration or geometry as desired or required to allow for the retainer 31 to be used with any make or model of equipment that may already be present in the user's laboratory (or to be compatible with future designs).

Although not shown, it should be appreciated that more than one cavity 33 may be provided within a given retainer 31. It should be appreciated that more than one wavelength access aperture 32 may be provided within a given cavity 33 (or other portion of a retainer device 31 if applicable). It should be appreciated that the access aperture 32 may be any size or shape as desired or required. It should be appreciated that if the retainer 31 does not include a cavity 33 then a wavelength access aperture 32 may be provided on a portion or location of the retainer device 31 to which would allow the scattering or diffraction beam to pass through the retainer 31 and intersect with the sample receptacle (not shown). Moreover, if there are multiple wavelength access apertures 32 then one or more wavelength apertures may be located in the cavity 33 of the retainer device 31 and one or more wavelength apertures may be located on a non-cavity portion of the retainer device 31.

Figure 15:
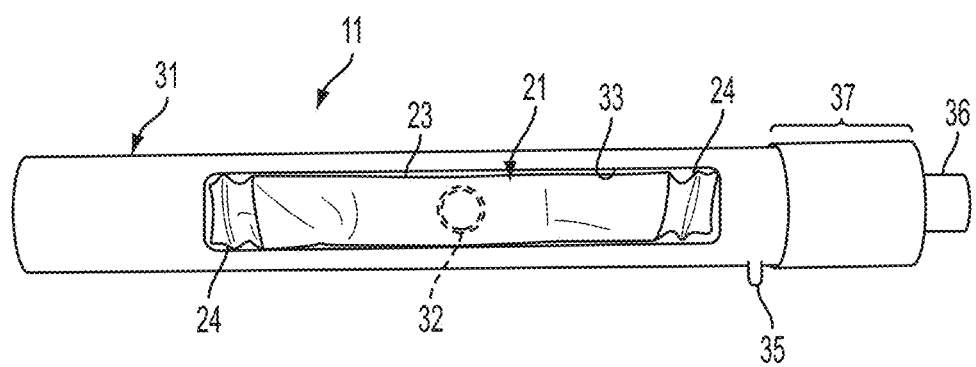
FIG. 15 provides a schematic illustration of an exemplary embodiment of the present invention sample holding device with a sample receptacle disposed therein.

FIG. 15 provides a schematic illustration of an aspect of an embodiment of the present invention sample holding device 11. A retainer 31 is in communication with a sample receptacle 21, which is located in a cavity 33 configured to receive the sample receptacle 21. The cavity 33 is configured to align the compartment 23 of the sample receptacle 21 with the wavelength access aperture 32 to allow a scattering or diffraction beam to pass through the compartment 23 and the sample. The wavelength access aperture 32 is indicated with dashed lines to delineate a location on the back side of the retainer 31 for this particular view of the illustration. Seals 24 at either end of the compartment 23 ensure that the sample (not shown) remains entrained in the sample receptacle 21 even if the device 11 is placed in a vacuum or other environment that could potentially degrade or contaminate the sample. Seals 24 at either end of the compartment 23 ensure that the sample (not shown) remains entrained even if the device 11, retainer 31, or sample receptacle 21 is moved, jarred or transported. The retainer 31 in this specific, non-limiting, example is configured to have an alignment pin 35 and alignment cap 37 to allow the retainer 31 to interact with other laboratory equipment that is used during beam scattering and diffraction testing. The retainer 31 also features a retrieval pin 36 to allow easy removal of the retainer 31 from the beam scattering and diffraction test equipment.

Figure 16:
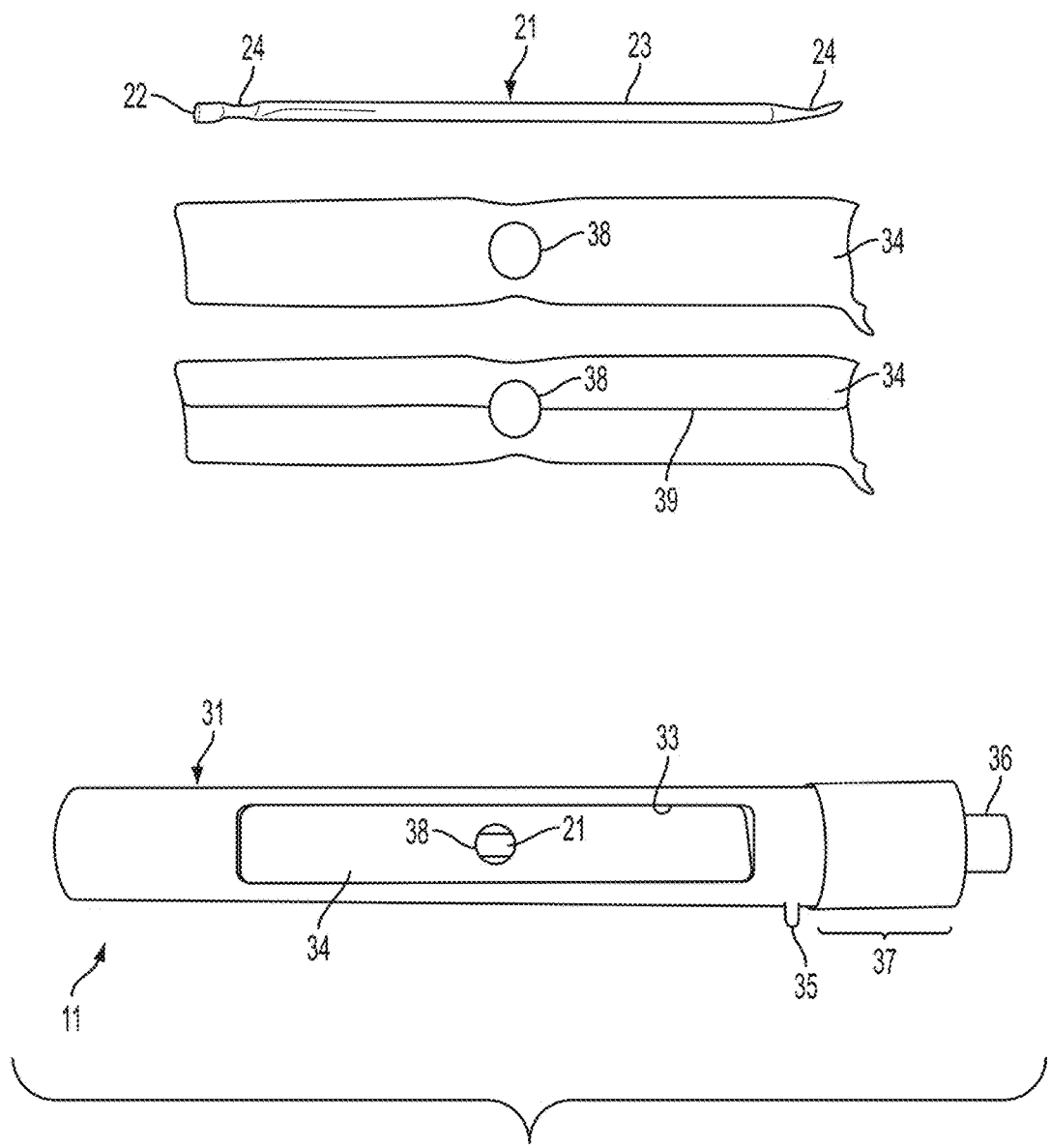
FIG. 16 provides a schematic illustration of an exemplary embodiment of the present invention sample holding device and exemplary constituent parts.

FIG. 16 provides a schematic illustration of an aspect of an embodiment of the present invention sample holding device 11 and some exemplary constituent parts. A sample receptacle 21 with a compartment 23, seals 24, and an access aperture 22 may be configured to be received by two adapters or inserts 34. The adapters or inserts 34 are configured with adapter apertures 38, and at least one of the adapters or inserts 34 may be configured to have a depression or crease 39 configured to receive the sample receptacle 21. A retainer 31, featuring an alignment pin 35, alignment cap 37, and a retrieval pin 36, has a cavity 33 that may be configured to accept the sample receptacle 21 which is sandwiched between the two adapters or inserts 34. When assembled, the adapter apertures 38 of the adapters or inserts 34 are aligned with the wavelength access aperture (not shown) of the retainer 31 to allow a scattering beam to pass unhindered through the sample receptacle 21. It should be appreciated that more than one adapter aperture 38 may be provided within a given adapter or insert 34. It should be appreciated that the adapter aperture 38 may be any size or shape as desired or required. It should be appreciated that one or more adapters or inserts 34 may be utilized for a given retainer 31.

Figure 17:
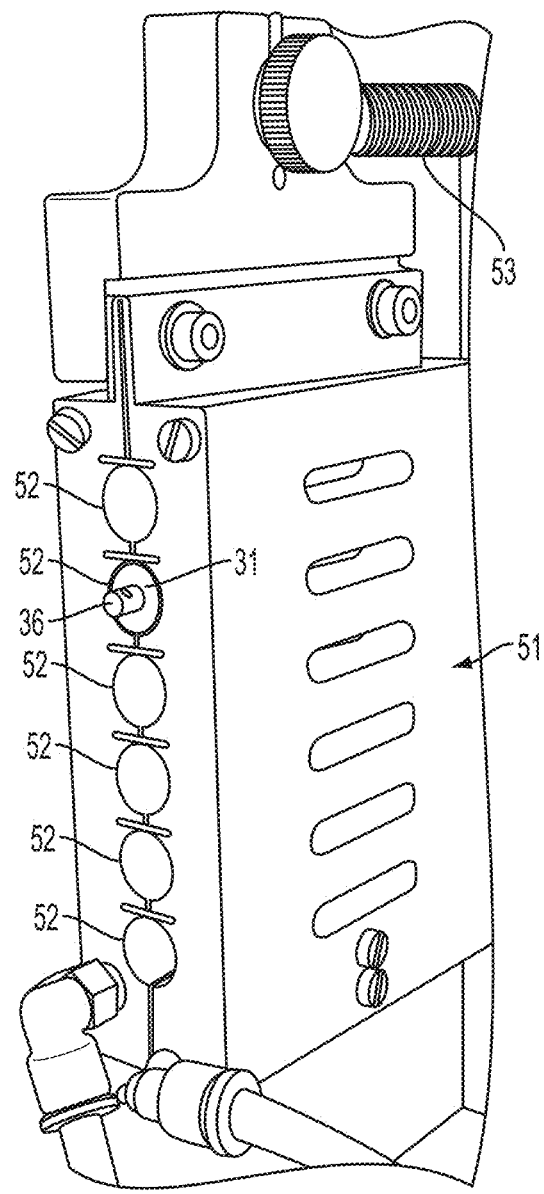
FIG. 17 provides a schematic illustration of an exemplary embodiment of the present invention sample holding device in an exemplary moveable rack.

FIG. 17 provides a schematic illustration of an aspect of an embodiment of the present invention sample holding device in an exemplary moveable rack 51. A linear rack 51 with multiple bays 52 is shown with a retainer 31 housed in one of the bays 52. The removal pin 36 of the retainer 31 is visible protruding out from the bay 52. The rack 51 is in communication with a track or feed mechanism 53 to allow for translation of the rack 51 so that multiple samples in the several bays 52 may be tested in sequence. It should be appreciated that the track or feed mechanism 53 may take any number of forms or configurations including, but not limited to, feed screws, tracks, racks, chains, belts, or helical screws.

It should be appreciated that any of the components or portions of the related components as discussed herein may take on all shapes along the entire continual geometric spectrum of manipulation of x, y and z planes to provide and meet the structural demands and operational requirements.

It should be appreciated that various sizes, dimensions, contours, rigidity, shapes, flexibility and materials of any of the components or portions of components in the various embodiments discussed throughout may be varied and utilized as desired or required.

An aspect of various embodiments of the present invention sample holding device (and related systems and methods) may provide a number of advantages. For instance, the related materials of the sample receptacle are robust and resist fracture and breakage. The sample receptacle is easy to access, as well as to load and remove specimens or other materials therefrom. Similarly, the retainer is easy to access, as well as to load and remove sample receptacles therefrom. Still yet, the retainer and/or sample receptacle are easy to load and remove from the rack or other device, system or mechanism. Moreover, the sample receptacle and related components and/or the retainer and related components may provide a vacuum tight seal. Furthermore, it should be appreciated that the sample receptacle and related components and/or the retainer and related components can be easy to use with numerous different types of systems which may incorporate x-rays, gamma rays, ultraviolet light, visible light, infrared light, or any other wavelength or frequency of the electromagnetic spectrum that may be desired or required by the user. The various components of the sample holding device may be readily transported either individually or collectively (or both), or practiced in a permanent facility or mobile facility (or both).

EXAMPLES

Practice of an aspect of an embodiment (or embodiments) of the invention will be still more fully understood from the following examples and experimental results, which are presented herein for illustration only and should not be construed as limiting the invention in any way.

Example and Experimental Results Set No. 1

Figure 18:
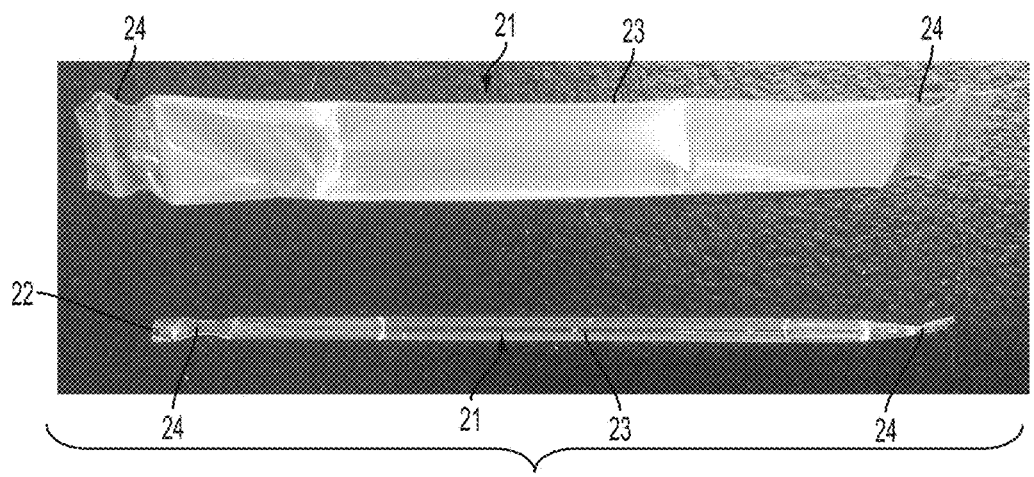
FIG. 18 provides a photographic depiction of an exemplary embodiment of the present invention sample receptacle that includes two seals, wherein the sample receptacle and both seals are made of the same material as a whole in a single piece.

FIG. 18 provides a photographic depiction of an exemplary embodiment of the present invention sample receptacle 21 that includes two seals 24, wherein the sample receptacle 21 and both seals 24 are made of the same material as a whole in a single piece.

As shown, the sample receptacle 21 may take any number of shapes or sizes as desired or required. In particular, a larger sample receptacle 21 (illustrated at the top of the figure relative to the bottom of the figure) may be used for samples (not shown) which are larger or easy to procure, while smaller sample receptacles 21 (illustrated at the bottom of the figure relative to the top of the figure) may be used for samples (not shown) which are harder to procure or produce. Regardless of the shape or size, the sample receptacle 21 will be comprised of a compartment 23 and one or more seals 24. In this example, the sample receptacle 21 and both seals 24 are made of the same plastic material as a whole in a single piece. In this example, both seals 24 are independent from the retainer 31. Optionally, the sample receptacle 21 may include one or more access apertures 22 which allows for insertion and removal of the sample from the compartment or compartments 23.

Figure 19:
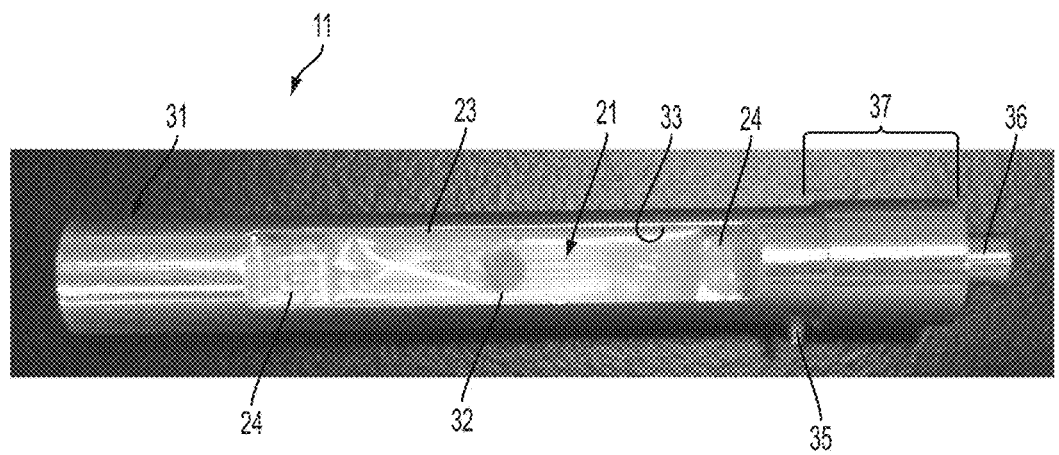
FIG. 19 provides a photographic depiction of an exemplary embodiment of the present invention sample holding device that includes a retainer and a sample receptacle (of which includes two seals) that is disposed in the retainer; wherein the sample receptacle and both seals are made of the same material as a whole in a single piece.

FIG. 19 provides a photographic depiction of an exemplary embodiment of the present invention sample holding device 11 that includes a retainer 31 and sample receptacle 21 (of which includes two seals 24) that is disposed in the retainer 31. The sample receptacle 21 and both seals 24 are made of the same material as a whole in a single piece. As shown, the retainer 31 is in communication with a sample receptacle 21, which is located in a cavity 33 configured to receive the sample receptacle 21. The cavity 33 is configured to align the compartment 23 of the sample receptacle 21 with the wavelength access aperture 32 to allow a scattering or diffraction beam to pass through the compartment 23 and the sample. The wavelength access aperture 32 is indicated with dashed lines to delineate a location on the back side of the retainer 31 for this particular view of the illustration. Seals 24 at either end of the compartment 23 ensure that the sample (not shown) remains entrained in the sample receptacle 21 even if the device 11 is placed in a vacuum or other environment that could potentially degrade or contaminate the sample. Seals 24 at either end of the compartment 23 ensure that the sample (not shown) remains entrained even if the device 11, retainer 31, or sample receptacle 21 is moved, jarred or transported. In this example, the sample receptacle 21 and both seals 24 are made of the same plastic material as a whole in a single piece. In this example, both seals 24 are independent from the retainer 31. The retainer 31 in this specific, non-limiting, example is configured to have an alignment pin 35 and alignment cap 37 to allow the retainer 31 to interact with other laboratory equipment that is used during beam scattering and diffraction testing. The retainer 31 also features a retrieval pin 36 to allow easy removal of the retainer 31 from the beam scattering and diffraction test equipment.

Still referring to FIGS. 18 and 19, the sample receptacle 21 may be a thin-wall x-ray absorption plastic tubing (or alternatively a polymer tubing, or the like) for solution x-ray scattering, but not limited thereto. Advantages of this aspect (approach) are, but not limited thereto, the following: (i) low-cost, (ii) robust material, (iii) easy to load, (iv) easy to seal (by thermal impulse sealer, (v) provides a vacuum-tight seal, to at least $5 \times 10^{-3}$ Torr. This last feature increases greatly the utility of x-ray solution scattering for anaerobic and other controlled atmosphere samples, as they can be prepared and loaded in the appropriate environment, and then safely conveyed to the instrument.

The non-limiting exemplary prototype of retainer 31 configuration may be applicable for, but not limited thereto, x-ray solution scattering or diffraction instrument. This illustrated prototype is only a single representative example, as the use of samples contained within x-ray transparent plastic tubing, mounted on a retainer 31 for data collection, is readily extendable to any x-ray solution scattering or diffraction instrumentation platform.

One of the novel aspects, but not limited thereto, of the method (and related device) presented herein is that it seals the entire sample into x-ray transparent plastic, therefore protecting it from the environment in the retainer 31. The new method (and related device) of sealing the sample into the sample receptacle tubing 21 is that it prevents the direct exposure of the sample to unwanted conditions like high vacuum or air. This new method (and related device) also reduces the chances of sample to sample cross contamination, which is a potential problem with current SAXS setups utilizing flowcells. Also, significantly, the plastic of the sample receptacle and seals as practiced in the present embodiment is a much more robust and resilient material than the thin-wall glass or quartz tubing currently utilized as sample vessels in solution x-ray scattering instruments.

It should be appreciated that sample receptacles 21 and retainers 11 can be fabricated for any instrument. Current designs of sample holders for x-ray scattering usually employ a glass or quartz tube, which can be either a capillary or a small diameter flow cell. These current sample holders are non-disposable therefore requiring cleaning to prevent cross-contamination between samples. In the experience of the present inventor, extended use of such sample holders is problematic and can become very expensive due to frequent replacement of a non-disposable product.

Current designs are also flawed in sealing the sample. Due to the high melting temperature of glass and quartz, heat sealing those vessels is dangerous to the sample and the heat treatment of the glass may weaken it. In other current design setups the capillary is sealed with a screw cap, which can develop leaks again jeopardizing the sample.

Due to these issues the present inventor sought a new sample holder vessel, which may be similar in diameter and x-ray transparency to vessels previously used, but different in melting temperature and fragility among other features. The present inventor was able to provide a plastic sample receptacle tubing 21, which has been shown to be x-ray transparent. This sample receptacle tubing 21, when heat sealed, safely contains the sample and can withstand the conditions most hutches would require, including high vacuum and alternate gases (e.g., helium, etc.).

The problem with the original metal cylinder Rigaku sample holder was that the sample holder capillary was permanently fixed inside the bore of the cylinder. Because of the inaccessibility of the capillary inside the metal cylinder, it was very difficult to load it and it was impossible to clean or exchange for another one. Another issue was that the sample holder was also extremely fragile and expensive to replace.

Accordingly, the present inventor resolved these issues, among others, by eliminating the capillary holder hole in the barrel of the round cylindrical unit and machining (or creating by other means) a rectangular cavity into the left side of the cylinder. The location of this rectangular indentation is centered on the x-ray porthole. This design of an embodiment of the present invention allows for, among other things, the holder to retain its ability to be temperature controlled while providing a space to secure a sample in it. The sample enclosed in either capillary or sealed tubing, with maximum length of 1.4," then fits into the new sample holder while remaining disposable therefore eliminating all or most of the issues with the Rigaku design.

The outside dimensions of the metal adapter are dictated by the temperature controlled chamber of the instrument. The dimension of the cavity inside the adapter was designed so that sample holders up to 0.215" diameter can fit it. If sample receptacle tubing that is used is less than 0.2" diameter, then putty (or some other material) may be necessary to secure the sample holder into the adapter. The present inventor tested a number of different varieties of sample receptacle tubings to find the optimal one. The sample receptacle tubing that the inventor found associated with an embodiment, with the least amount of inherent x-ray scatter is: Advanced Polymers PN-041100cst with ID of 0.041" and wall=0.0010. The present inventor heat sealed the sample into the sample receptacle tubing, therefore immobilizing it. This sample receptacle tubing could withstand the $5 \times 10^{-3}$ Torr vacuum repeatedly without having any x-ray scattering or sample leakage.

ADDITIONAL EXAMPLES

Practice of an aspect of an embodiment (or embodiments) of the invention will be still more fully understood from the following examples, which are presented herein for illustration only and should not be construed as limiting the invention in any way.

Example 1

A device for use in solution scattering or diffraction, the device comprising: at least one sample receptacle comprising, at least in part, a polymer material, polymeric material, cellulose material, cellulosic material, or any combination thereof, the at least one sample receptacle configured to accommodate a sample; a retainer, the retainer configured to removably hold the at least one sample receptacle and allow for the at least one sample receptacle to be in communication with a scattering beam or diffraction beam; and wherein the at least one sample receptacle is configured to be sealable for containing the sample, wherein sealing is independent of the retainer.

Example 2

The device of example 1, wherein the scattering beam or diffraction beam is an x-ray beam.

Example 3

The device of example 1 (as well as subject matter of example 2), wherein each of the at least one sample receptacles comprises one or more access apertures.

Example 4

The device of example 1 (as well as subject matter of one or more of any combination of examples 2-3), wherein each of the at least one sample receptacles comprises one or more compartments.

Example 5

The device of example 1 (as well as subject matter of one or more of any combination of examples 2-4), wherein the sealing of at least one the sample receptacle comprises one or more of any combination of the following: heat seal, mechanical seal, adhesion seal, or chemical seal.

Example 6

The device of example 1 (as well as subject matter of one or more of any combination of examples 2-5), wherein the at least one sample receptacle is compatible with gamma wavelengths, x-ray wavelengths, ultraviolet wavelengths, visible wavelengths, or infrared wavelengths.

Example 7

The device of example 1 (as well as subject matter of one or more of any combination of examples 2-6), wherein the at least one sample receptacle is opaque to visible wavelengths.

Example 8

The device of example 1 (as well as subject matter of one or more of any combination of examples 2-7), wherein the at least one sample receptacle is translucent or transparent to x-ray wavelengths.

Example 9

The device of example 1 (as well as subject matter of one or more of any combination of examples 2-8), wherein the at least one sample receptacle comprising a plurality of compartments.

Example 10

The device of example 1 (as well as subject matter of one or more of any combination of examples 2-9), wherein the sample receptacle is configured to allow for recovery of the sample from the sample receptacle.

Example 11

The device of example 1 (as well as subject matter of one or more of any combination of examples 2-10), wherein the at least one sample receptacle is disposable.

Example 12

The device of example 1 (as well as subject matter of one or more of any combination of examples 2-11), wherein the retainer configured to hold at least one of the sample receptacles by one or more of any combination of the retention modes: friction fit retention, interference fit retention, magnetic retention, mechanical retention, or adhesive retention.

Example 13

The device of example 1 (as well as subject matter of one or more of any combination of examples 2-12), wherein the retainer is disposable.

Example 14

The device of example 1 (as well as subject matter of one or more of any combination of examples 2-13), further comprising a rack to hold the retainer.

Example 15

The device of example 1 (as well as subject matter of one or more of any combination of examples 2-14), wherein the rack is configured to hold a plurality of the retainers.

Example 16

The device of example 1 (as well as subject matter of one or more of any combination of examples 2-15), wherein the rack is configured to align the plurality of retainers linearly.

Example 17

The device of example 1 (as well as subject matter of one or more of any combination of examples 2-15), wherein the rack is configured to align the plurality of retainers curvilinearly.

Example 18

The device of example 16 (as well as subject matter of one or more of any combination of examples 2-17), wherein the curvilinear alignment includes circular, semi-circular, oval, elliptical, parabolic, hyperbolic, or semi-oval.

Example 19

The device of example 1 (as well as subject matter of one or more of any combination of examples 2-18), wherein the rack is configured to allow pivoting of one or more of the retainers with respect to one or more of other the retainers.

Example 20

The device of example 1 (as well as subject matter of one or more of any combination of examples 2-19), further comprising: a scattering system or diffraction system, or both a scattering and diffraction system. The scattering or diffraction system comprising: a source configured to pass a scattering beam or diffraction beam through the at least one sample receptacle; and a detector configured to receive a scattered beam or diffracted beam exiting from the at least one sample receptacle.

Example 21

The device of example 20 (as well as subject matter of one or more of any combination of examples 2-19), wherein the scattering system or diffraction system is an x-ray system.

Example 22

The device of example 20 (as well as subject matter of one or more of any combination of examples 2-19 and 21), wherein the scattering system or diffraction system is a gamma system, ultraviolet system, visible system, or infrared system.

Example 23

The device of example 1 (as well as subject matter of one or more of any combination of examples 2-19 and 21-22), wherein the at least one sample receptacle is configured in at least one or more of the following shapes: spherical, cubical, cuboid, prismatic, pyramidal, tubular, or cylindrical.

Example 24

A method for solution scattering or diffraction, the method comprising: providing at least one sample receptacle comprising, at least in part, a polymer material, polymeric material, cellulose material, cellulosic material, or any combination thereof, the at least one sample receptacle accommodating a sample; holding the at least one sample receptacle and allowing for the at least one sample receptacle to be in communication with a scattering beam or diffraction beam; and sealing the at least one sample receptacle for containing the sample.

Example 25

The method of example 24, wherein the scattering beam or diffraction beam comprises x-ray wavelengths.

Example 26

The method of example 24 (as well as subject matter of example 25), wherein the scattering beam or diffraction beam comprises gamma, ultraviolet, visible, or infrared wavelengths.

Example 27

The method of example 24 (as well as subject matter of one or more of any combination of examples 25-26), wherein the holding is provided by a retainer, wherein the retainer is configured to removably hold the at least one sample receptacle.

Example 28

The method of example 24 (as well as subject matter of one or more of any combination of examples 25-27), wherein the sealing of the at least one sample receptacle is independent of the retainer.

Example 29

The method of example 24 (as well as subject matter of one or more of any combination of examples 25-28), wherein the sealing of the at least one sample receptacle is dependent upon the retainer.

Example 30

The method of example 24 (as well as subject matter of one or more of any combination of examples 25-29), wherein the accommodation is provided by inserting the sample into the at least one sample receptacle through one or more access apertures of the at least one sample receptacle.

Example 31

The method of example 24 (as well as subject matter of one or more of any combination of examples 25-30), wherein the sealing of at least one the sample receptacles comprises one or more of any combination of the following: heat seal, mechanical seal, adhesion seal, or chemical seal.

Example 32

The method of example 24 (as well as subject matter of one or more of any combination of examples 25-31), wherein the at least one sample receptacle is compatible with gamma wavelengths, x-ray wavelengths, ultraviolet wavelengths, visible wavelengths, or infrared wavelengths.

Example 33

The method of example 24 (as well as subject matter of one or more of any combination of examples 25-32), further comprising: recovering the sample from the sample receptacle.

Example 34

The method of example 24 (as well as subject matter of one or more of any combination of examples 25-33), further comprising loading one or more of the retainers into a rack.

Example 35

The method of example 24 (as well as subject matter of one or more of any combination of examples 25-34), further comprising: passing a scattering beam or diffraction beam through the at least one sample receptacle; and receiving and detecting a scattered beam or diffracted beam exiting from the at least one sample receptacle.

Example 36

A method for solution scattering or diffraction, the method comprising: providing at least one sample receptacle comprising, at least in part, a polymer material, polymeric material, cellulose material, cellulosic material, or any combination thereof, the at least one sample receptacle configured to accommodate a sample; providing a retainer configured for holding the at least one sample receptacle and allowing for the at least one sample receptacle to be in communication with a scattering beam or diffraction beam; and the sample receptacle configured to allow the sample to be sealed in the at least one sample receptacle for containing the sample.

Example 37

The method of example 36, wherein the scattering beam or diffraction beam comprises x-ray wavelengths.

Example 38

The method of example 36 (as well as subject matter of example 37), wherein the scattering beam or diffraction beam comprises gamma, ultraviolet, visible, or infrared wavelengths.

Example 39

The method of example 36 (as well as subject matter of one or more of any combination of examples 37-38), wherein the holding is provided to removably hold the at least one sample receptacle.

Example 40

The method of example 36 (as well as subject matter of one or more of any combination of examples 37-39), wherein the sealing of the at least one sample receptacle is independent of the retainer.

Example 41

The method of example 36 (as well as subject matter of one or more of any combination of examples 37-40), wherein the sealing of the at least one sample receptacle is dependent upon the retainer.

Example 42

A method for solution scattering or diffraction, the method comprising: providing at least one sample receptacle comprising, at least in part, a polymer material, polymeric material, cellulose material, cellulosic material, or any combination thereof, the at least one sample receptacle configured to accommodate a sample; wherein the at least one sample receptacle is configured to allow the at least one sample receptacle to be in communication with a scattering beam or diffraction beam; and the sample receptacle configured to allow the sample to be sealed in the at least one sample receptacle for containing the sample.

Example 43

The device of example 1 (as well as subject matter of one or more of any combination of examples 2-23), wherein said scattering beam or diffraction beam is one or more of the following: gamma beam, ultraviolet beam, visible beam, or infrared beam.

Example 44

The device of example 43 (as well as subject matter of one or more of any combination of examples 2-23), wherein said scattering beam or diffraction beam further comprises an x-ray beam.

Example 45

The method of examples 24-35, 36-41, or 42, further comprising using any of the components (of the devices or systems) provided in any one or more of examples 1-23 and 43-44.

Example 46

The method of manufacturing any of the components (of the devices or systems) provided in any one or more of examples 1-23 and 43-44.

REFERENCES

The devices, systems, compositions, components, and methods of various embodiments of the invention disclosed herein may utilize aspects disclosed in the following references, applications, publications and patents and which are hereby incorporated by reference herein in their entirety (and which are not admitted to be prior art with respect to the present invention by inclusion in this section):

1. U.S. Patent Application Publication No. US 2013/0101091 A1, Garvey, et al., "Sealed Detector Array for the Collection of Both Wide Angle and Small Angle X-ray Scattering", Apr. 28, 2013.
2. International Patent Application No. WO 2013/025737 A1, Garvey, et al., "Sealed Detector Array for the Collection of Both Wide Angle and Small Angle X-ray Scattering.
3. U.S. Patent Application Serial No. US 2011/0135990 A1, Yamamoto, et al., "Sodium Secondary Battery", Jun. 9, 2011.
4. Lipfert, J., et al., "Sample holder for small-angle x-ray scattering static and flow cell measurements", Rev. Sci. Instrum. 77,046108, (2006), pp. 1-3.
5. Toft, K., et al., "High-Throughput Small Angle X-ray Scattering from Proteins in Solution Using a Microfluidic Front-End", Analytical Chemistry, Vol. 80, No. 10, May 15, 2008, pp. 3648-3654.
6. Soliman, A., et al., "Development of high-performance X-ray transparent crystallization plates for in situ protein crystal screening and analysis", Acta Crys. (2011), D67, pp. 646-656.
7. Kalinin, Y., et al., "Crystal growth in X-ray-transparent plastic tubing: an alternative for high-throughput applications", Acta Cryst. (2005), D61, pp. 1528-1532.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A device for use in solution scattering or diffraction, said device comprising:
    at least one sample receptacle comprising at least one seal;
    wherein said receptacle and said at least one seal are made as a single piece of the same material;
    wherein said whole single piece of the same material comprise a polymer material, polymeric material, cellulose material, cellulosic material, or any combination thereof;
    wherein said at least one sample receptacle configured to accommodate a sample;
    a retainer, said retainer configured to removably hold said at least one sample receptacle and allow for said at least one sample receptacle to be in communication with a scattering beam or diffraction beam; and
    wherein said at least one sample receptacle is configured to be sealable for containing the sample, wherein sealing is independent of said retainer.

2. The device of claim 1, wherein said scattering beam or diffraction beam is an x-ray beam.

3. The device of claim 1, wherein each of said at least one sample receptacles comprises one or more access apertures.

4. The device of claim 1, wherein each of said at least one sample receptacles comprises one or more compartments.

5. The device of claim 1, wherein said sealing of at least one said sample receptacle comprises one or more of any combination of the following: heat seal, mechanical seal, adhesion seal, or chemical seal.

6. The device of claim 1, wherein said at least one sample receptacle is compatible with gamma wavelengths, x-ray wavelengths, ultraviolet wavelengths, visible wavelengths, or infrared wavelengths.

7. The device of claim 1, wherein said at least one sample receptacle is opaque to visible wavelengths.

8. The device of claim 1, wherein said at least one sample receptacle is translucent or transparent to x-ray wavelengths.

9. The device of claim 1, wherein said at least one sample receptacle comprises a plurality of compartments.

10. The device of claim 1, wherein said sample receptacle is configured to allow for recovery of the sample from said sample receptacle.

11. The device of claim 1, wherein said at least one sample receptacle is disposable.

12. The device of claim 1, wherein said retainer is configured to hold at least one of said sample receptacles by one or more of any combination of the retention modes: friction fit retention, interference fit retention, magnetic retention, mechanical retention, or adhesive retention.

13. The device of claim 1, wherein said retainer is disposable.

14. The device of claim 1, further comprising a rack to hold said retainer.

15. The device of claim 14, wherein said rack is configured to hold a plurality of retainers.

16. The device of claim 15, wherein said rack is configured to align said plurality of retainers linearly.

17. The device of claim 15, wherein said rack is configured to align said plurality of retainers curvilinearly.

18. The device of claim 17, wherein said rack is configured to align said plurality of retainers circularly, semicircularly, ovally, elliptically, parabolically, hyperbolically, or semi-ovally.

19. The device of claim 15, wherein said rack is configured to allow pivoting of one or more of said plurality of retainers with respect to one or more of other said plurality of retainers.

20. The device of claim 1, further comprising:
    a scattering system or diffraction system, or both a scattering and diffraction system, said scattering or diffraction system comprising:
        a source configured to pass a scattering beam or diffraction beam through said at least one sample receptacle; and
        a detector configured to receive a scattered beam or diffracted beam exiting from said at least one sample receptacle.

21. The device of claim 20, wherein said scattering system or diffraction system is an x-ray system.

22. The device of claim 20, wherein said scattering system or diffraction system is a gamma system, ultraviolet system, visible system, or infrared system.

23. The device of claim 1, wherein said at least one sample receptacle is configured in at least one or more of the following shapes: spherical, cubical, cuboid, prismatic, pyramidal, tubular, or cylindrical.

24. A method for solution scattering or diffraction, said method comprising:
    providing at least one sample receptacle comprising at least one seal;

wherein said receptacle and said at least one seal are made as a single piece of the same material;

wherein said whole single piece of the same material comprise a polymer material, polymeric material, cellulose material, cellulosic material, or any combination thereof;

wherein said at least one sample receptacle configured for accommodating a sample;

holding said at least one sample receptacle with a retainer and allowing for said at least one sample receptacle to be in communication with a scattering beam or diffraction beam; and sealing said at least one sample receptacle for containing the sample, wherein said sealing is independent of said retainer.

25. The method of claim 24, wherein said scattering beam or diffraction beam comprises x-ray wavelengths.

26. The method of claim 24, wherein said scattering beam or diffraction beam comprises gamma, ultraviolet, visible, or infrared wavelengths.

27. The method of claim 24, wherein said retainer is configured to removably hold said at least one sample receptacle.

28. The method of claim 24, wherein said accommodation is provided by inserting the sample into said at least one sample receptacle through one or more access apertures of said at least one sample receptacle.

29. The method of claim 24, wherein said sealing of at least one said sample receptacles comprises one or more of any combination of the following: heat seal, mechanical seal, adhesion seal, or chemical seal.

30. The method of claim 24, wherein said at least one sample receptacle is compatible with gamma wavelengths, x-ray wavelengths, ultraviolet wavelengths, visible wavelengths, or infrared wavelengths.

31. The method of claim 24, further comprising: recovering the sample from said sample receptacle.

32. The method of claim 24, further comprising loading one or more of said retainers into a rack.

33. The method of claim 24, further comprising:
passing a scattering beam or diffraction beam through said at least one sample receptacle; and
receiving and detecting a scattered beam or diffracted beam exiting from said at least one sample receptacle.

34. A method for solution scattering or diffraction, said method comprising:
providing at least one sample receptacle comprising at least one seal;
wherein said receptacle and said at least one seal are made as a single piece of the same material;
wherein said whole single piece of the same material comprise a polymer material, polymeric material, cellulose material, cellulosic material, or any combination thereof;
wherein said at least one sample receptacle configured to accommodate a sample;
providing a retainer configured for holding said at least one sample receptacle and allowing for said at least one sample receptacle to be in communication with a scattering beam or diffraction beam; and
sealing said at least one sample receptacle for containing the sample, wherein sealing is independent of said retainer.

35. The method of claim 34, wherein said scattering beam or diffraction beam comprises x-ray wavelengths.

36. The method of claim 34, wherein said scattering beam or diffraction beam comprises gamma, ultraviolet, visible, or infrared wavelengths.

37. The method of claim 34, wherein said holding is provided to removably hold said at least one sample receptacle.

38. The method of claim 34, further comprising:
passing a scattering beam or diffraction beam through said at least one sample receptacle; and
receiving and detecting a scattered beam or diffracted beam exiting from said at least one sample receptacle.

* * * * *